US012045070B2

(12) United States Patent
Ma et al.

(10) Patent No.: US 12,045,070 B2
(45) Date of Patent: Jul. 23, 2024

(54) BREEDING ROBOT AND METHOD

(71) Applicant: Institute of Urban Agriculture, Chinese Academy of Agricultural Sciences, Chengdu (CN)

(72) Inventors: Wei Ma, Chengdu (CN); Qichang Yang, Chengdu (CN)

(73) Assignee: INSTITUTE OF URBAN AGRICULTURE, CHINESE ACADEMY OF AGRICULTURAL SCIENCES, Chengdu (CN)

( * ) Notice: Subject to any disclaimer, the term of this patent is extended or adjusted under 35 U.S.C. 154(b) by 0 days.

(21) Appl. No.: 18/344,889

(22) Filed: Jun. 30, 2023

(65) Prior Publication Data
US 2024/0160228 A1    May 16, 2024

(30) Foreign Application Priority Data
Jul. 20, 2022  (CN) .......................... 202210859368.8

(51) Int. Cl.
| A01G 7/00 | (2006.01) |
| A01G 3/037 | (2006.01) |
| A01H 1/02 | (2006.01) |
| G05D 1/243 | (2024.01) |
| G05D 1/248 | (2024.01) |
| G05D 1/648 | (2024.01) |
| G05D 1/656 | (2024.01) |

(Continued)

(52) U.S. Cl.
CPC ............. *G05D 1/656* (2024.01); *A01G 3/037* (2013.01); *A01H 1/027* (2021.01); *G05D 1/243* (2024.01); *G05D 1/248* (2024.01); *G05D 1/648* (2024.01); *G05D 2105/15* (2024.01); *G05D 2107/21* (2024.01); *G05D 2109/12* (2024.01); *G05D 2111/10* (2024.01)

(58) Field of Classification Search
CPC .......... A01H 1/027; A01H 1/02; A01G 3/037; A01G 3/033; G05D 1/656; G05D 1/248; G05D 1/243; B25J 5/007; B25J 9/1679
See application file for complete search history.

(56) References Cited

U.S. PATENT DOCUMENTS 4,087,937 A * 5/1978 Meader ................. A01H 1/027
47/1.41

FOREIGN PATENT DOCUMENTS

| CN | 108326823 A | 7/2018 |
| CN | 109042306 A * | 12/2018 | ............. A01H 1/027 |

(Continued)

*Primary Examiner* — Trinh T Nguyen
(74) *Attorney, Agent, or Firm* — Bayramoglu Law Offices LLC

(57) ABSTRACT

A breeding robot including a base and a support being movably connected to the base. The support is of a hollow cylindrical structure, a telescopic arm movably passes through the support, a first motor is mounted to an end of the telescopic arm away from the support, a transmission shaft of the first motor is connected to a rotating bracket, a saw blade is mounted to the bottom side of the rotating bracket, and the saw blade is used for cutting maize tassel. The end of the rotating bracket is mounted with a CCD detector, and the CCD detector is used for detecting the position of the maize tassel. A blower is further mounted to the base, an air outlet of the blower is connected to a first end of an air duct, and a second end of the air duct is connected to the air blowing portion.

10 Claims, 2 Drawing Sheets

(51) Int. Cl.
*G05D 105/15* (2024.01)
*G05D 107/20* (2024.01)
*G05D 109/12* (2024.01)
*G05D 111/10* (2024.01)

(56) References Cited

FOREIGN PATENT DOCUMENTS

| | | | | | |
|---|---|---|---|---|---|
| CN | 110692352 | A | * | 1/2020 | ............. A01C 15/00 |
| CN | 113207675 | A | * | 8/2021 | |
| CN | 113331050 | A | * | 9/2021 | |
| CN | 216438220 | U | | 5/2022 | |
| CN | 114885821 | A | * | 8/2022 | |
| CN | 116724885 | A | * | 9/2023 | |
| KR | 20190130208 | A | * | 11/2019 | |
| WO | WO-2018203337 | A1 | * | 11/2018 | ........... A01D 46/005 |

* cited by examiner

BREEDING ROBOT AND METHOD

CROSS-REFERENCE TO THE RELATED APPLICATION

This application is based upon and claims priority to Chinese Patent Application No. 202210859368.8 filed on Jul. 20, 2022, the entire content of which is incorporated herein by reference.

TECHNICAL FIELD

The present disclosure relates to the field of breeding technology, in particular to a breeding robot and method.

BACKGROUND

Maize breeding is a labor-intensive process. The most typical one is the emasculation of the maize itself, and the pollen of pollinated maize falls on the stamen of the maize to complete the pollination of hybrid maize.

In the prior art, emasculation and pollination are generally performed manually. However, it is labor-intensive and inefficient, and the economic cost is relatively high.

SUMMARY

In order to solve the above technical problem, the present disclosure provides a breeding robot and method.

The present disclosure provides a breeding robot comprising a base provided at the bottom with a walking device;
  a support is movably connected to the base; the support is of a hollow cylindrical structure, a telescopic arm movably passes through the support, a first motor is mounted to an end of the telescopic arm away from the support, a transmission shaft of the first motor is connected to a rotating bracket, a saw blade is mounted to the bottom side of the rotating bracket, and the saw blade is used for cutting maize tassel;
  a blower is further mounted to the base, an air outlet of the blower is connected to the first end of an air duct, and the second end of the air duct is connected to the air blowing portion;
  the end of the rotating bracket is mounted with a CCD detector, and the CCD detector is used for detecting the position of the maize tassel.

Optionally, a satellite positioning system is further mounted to the base, and a controller is provided in the base, and the controller is used for receiving an instruction of the satellite positioning system and controlling the operation of the walking device.

Optionally, the end of the rotating bracket away from the telescopic arm is provided with a second motor connected to the air blowing portion for adjusting an angle of the air blowing portion relative to the rotating bracket.

Optionally, a third motor is mounted in the support, a rotating shaft of the third motor is connected to one end of a lead screw, and the other end of the lead screw is threadedly connected to the telescopic arm, so that the telescopic arm moves up and down along the support.

Optionally, a fourth motor is mounted to the telescopic arm, and the transmission shaft of the fourth motor is connected to a cross bar, the cross bar being arranged transversely for shaking off pollens.

Optionally, the saw blade is detachably connected to the bottom side of the rotating bracket.

Optionally, a part of the air duct is erected on the support, the telescopic arm, and the rotating bracket.

Optionally, the controller is used for controlling a rotation of the first motor, the second motor, the third motor, and the blower to achieve emasculation and/or pollination.

Optionally, a folding bracket is further mounted to the support, the first end of the folding bracket being hinged to the support and the second end of the folding bracket being hinged to the base.

A breeding method based on the breeding robot, characterized by comprising steps as follows:
  S1: the CCD detector determines the position of emasculated maize and transmits the position to the controller, the controller controlling the walking device to walk to the position;
  S2: the controller controls the first motor to rotate a rotating bracket to drive a saw blade to perform emasculation;
  S3: the breeding robot returns;
  S4: the CCD detector determines the position of pollinating maize and transmits the position to the controller, and the controller controls the walking device to walk to the position;
  S5: the controller controls the blower to rotate, and the air blowing portion blows pollens;
  and S6: the breeding robot returns.

The technical solutions provided in the embodiments of the present disclosure have the following advantages compared to the prior art:

1, the present disclosure provides a breeding robot, comprising a base, wherein a walking device is provided at the bottom of the base, and the walking device drives the robot to move; a support is movably connected to the base; the support is of a hollow cylindrical structure, a telescopic arm movably passes through the support, a first motor is mounted to an end of the telescopic arm away from the support, a transmission shaft of the first motor is connected to a rotating bracket, a saw blade is mounted to the bottom side of the rotating bracket, and the saw blade is used for cutting maize tassel; the end of the rotating bracket is mounted with a CCD detector, and the CCD detector is used for detecting the position of the maize tassel; the present disclosure enables automatic emasculation through the provision of a saw blade and a CCD detector;

2, a blower is further mounted to the base, an air outlet of the blower is connected to the first end of an air duct, and the second end of the air duct is connected to the air blowing portion; by aligning the air blowing portion with the pollinating maize and blowing pollens, the pollination quality can be mechanically improved; and 3, through the emasculation work by the saw blade and the pollination work by the air blowing portion, the present disclosure achieves the mechanization of emasculation and pollination, improves productivity, and reduces costs.

BRIEF DESCRIPTION OF THE DRAWINGS

The drawings herein are incorporated into the description and form a part of the description, showing embodiments in conformity with the present disclosure, and are used together with the description to explain the principles of the present disclosure.

In order to illustrate the embodiments of the present disclosure or the technical solutions in the prior art more clearly, the following will briefly introduce the drawings that need to be used in the description of the embodiments or the prior art. Obviously, for those of ordinary skills in the art, other drawings can be obtained according to these drawings without involving inventive efforts.

Wherein: 1—base; 2—walking device; 3—support; 4—telescopic arm; 5—first motor; 6—rotating bracket; 7—saw blade; 8—blower; 9—air duct; 10—air blowing portion; 11—satellite positioning system; 12—crossbar; and 13—folding bracket.

DETAILED DESCRIPTION OF THE EMBODIMENTS

In order to better understand the above objectives, features, and advantages of the present disclosure, the following will further describe the scheme of the present disclosure. It should be noted that the embodiments and features of the embodiments of the present disclosure can be combined with each other without conflict.

Many specific details have been elaborated in the following description to facilitate a full understanding of the present disclosure, but the present disclosure can also be implemented in other ways different from those described here; obviously, the embodiments in the description are only a portion of the embodiments of the disclosure, rather than all the embodiments.

The present disclosure provides a breeding robot comprising a base 1 provided at the bottom with a walking device 2. The walking device 2 drives a robot to reach a specified position.

In order to achieve automatic walking of the robot, a satellite positioning system 11 is further mounted to the base 1, and a controller (not shown in the figure) is provided in the base 1, and the controller receives an instruction of the satellite positioning system 11 and controls the operation of the walking device 2. In this embodiment, the controller further includes a wireless receiving device. The position information of the robot obtained by satellite positioning system 11 is transmitted to the wireless receiving device, and then the controller controls the robot to walk to the specified position.

Figure 1:
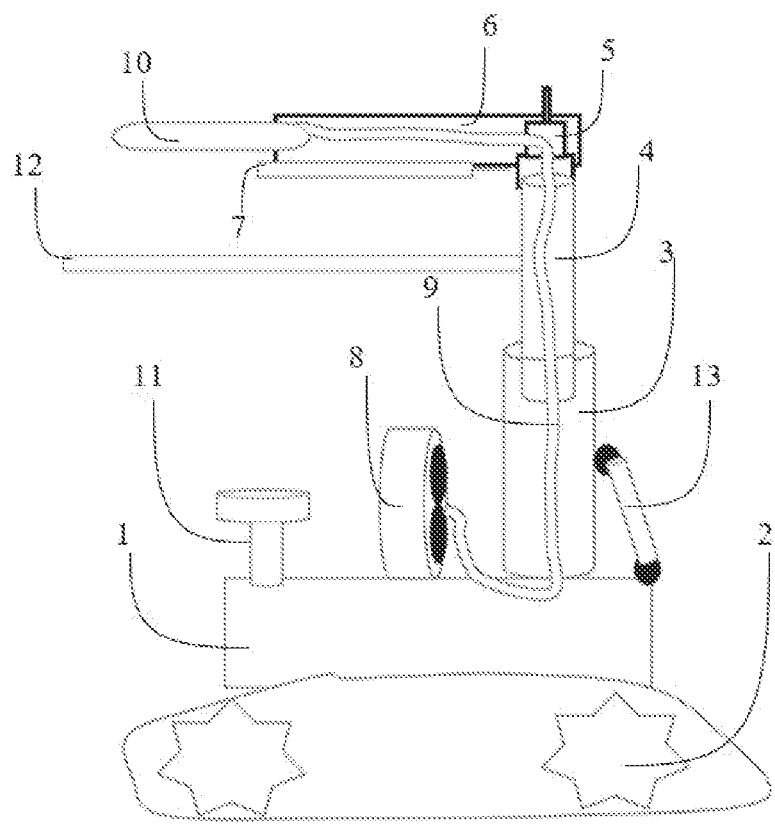
FIG. 1 is an overall structural diagram of a breeding robot according to an embodiment of the present disclosure.
Figure 2:
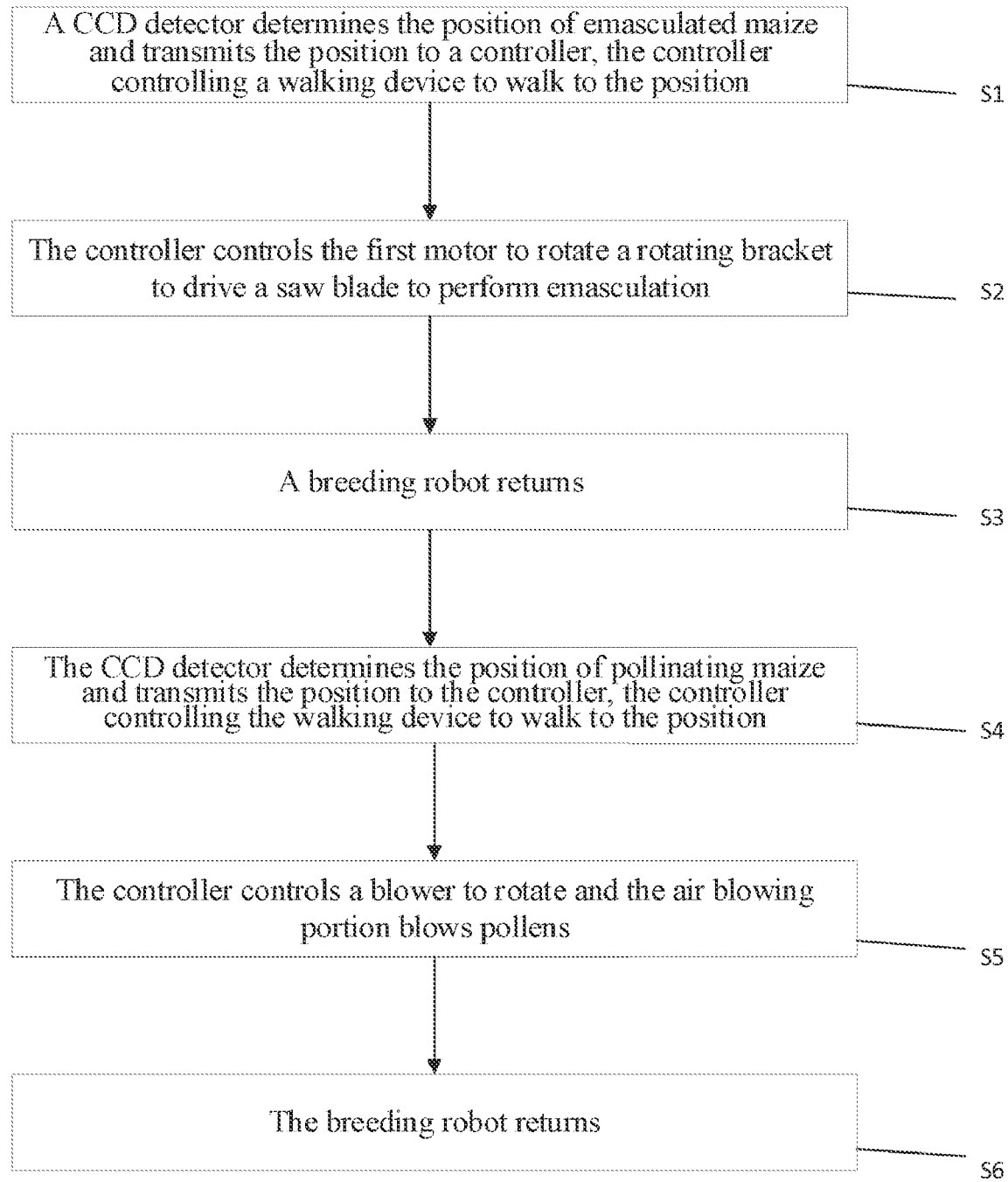
FIG. 2 is a flowchart of the breeding method according to an embodiment of the present disclosure.

This embodiment can achieve maize emasculation. As shown in FIG. 1, a support 3 is movably connected to the base 1. The support 3 is of a hollow cylindrical structure, a telescopic arm 4 movably passes through the support 3, and the telescopic arm 4 can move up and down along the support 3. The end of the telescopic arm 4 away from the support 3 is mounted with a first motor 5, a transmission shaft of the first motor 5 is connected to a rotating bracket 6, a saw blade 7 is mounted to the bottom side of the rotating bracket 6, and the saw blade 7 is used for cutting maize tassel. The up-and-down movement of the telescopic arm 4 can drive the up-and-down movement of the saw blade 7 to adapt the saw blade 7 to different maize tassel heights. After the saw blade 7 reaches a suitable height, the first motor 5 starts to work so that the rotating bracket 6 starts to rotate, and the rotation of the rotating bracket 6 drives the rotation of the saw blade 7, thereby achieving maize emasculation.

In order to achieve the up-and-down movement of the telescopic arm, in the present embodiment, a third motor (not shown in the figure) is mounted in the support 3, and a rotating shaft of the third motor is connected to one end of a lead screw, and the other end of the lead screw is threadedly connected to the telescopic arm 4, so that the telescopic arm 4 moves up and down along the support 3. When the position of the saw blade 7 needs to be adjusted, the controller controls the fourth motor to rotate, thereby driving the telescopic arm 4 to move up and down via the lead screw, and further adjusting the saw blade 7 to reach a suitable position.

This embodiment may also improve maize pollination quality. Specifically, a blower 8 is further mounted to the base 1, an air outlet of the blower 8 is connected to the first end of an air duct 9, the second end of the air duct 9 is connected to an air blowing portion 10, and the air blowing portion 10 is aligned with pollinating maize. When the blower 8 is turned on, the wind blows the pollen of pollinating maize through the air blowing portion 10, so that the pollination quality can be improved.

Further, a second motor (not shown in the figure) is provided at the end of the rotating bracket 6 away from the telescopic arm 4, and the second motor is connected to the air blowing portion 10 for adjusting the angle of the air blowing portion 10 with respect to the rotating bracket 6. The second motor is electrically connected to the controller. When the controller judges that the air outlet position of the air blowing portion 10 has a certain deviation from the pollinating maize, the controller controls the rotation of the second motor, adjusts the angle of the air blowing portion 10 relative to the rotating bracket 6, and further adjusts the air outlet position of the air blowing portion 10, so as to achieve the accurate control of pollination. Specifically, in the present embodiment, the angle range of the air blowing portion 10 with respect to the rotating bracket 6 is 40°, up or down by 200 each.

In order to further improve the quality of maize pollination, a cross bar 12 is mounted to the telescopic arm 4, a fourth motor (not shown in the figure) is mounted to the telescopic arm 4, the transmission shaft of the fourth motor is connected to the cross bar 12, and the cross bar 12 is transversely arranged for shaking off pollens. Specifically, a fourth motor is provided at the joint between the cross bar 12 and the telescopic arm 4, the rotating shaft of the fourth motor is connected to the cross rod 12, and the cross rod 12 can perform slow rotation and vibration under the drive of the fourth motor, and further serve the purpose of shaking off pollens while the air blowing portion 10 is blowing.

In addition, a CCD detector for detecting the position of maize tassel is mounted at the end of the rotating bracket 6. The first step in this embodiment is to acquire a CCD image of maize tassel to determine the position of the maize tassel. The second step is to calculate the deviation of the saw blade 7 from the target maize tassel according to the obtained CCD image. The third step is to determine the position adjustment amount of the telescopic arm 4 according to the deviation. The fourth step is to adjust the movement of the telescopic arm 4 according to the position adjustment amount of the telescopic arm 4 until the telescopic arm 4 has the same height as the target maize tassel. The fifth step is to control the movement of the saw blade 7 or the air blowing portion 10 to complete the emasculation or pollination of the maize.

In addition, the saw blade 7 in this embodiment is detachably connected to the bottom side of the rotating bracket 6. When only maize pollination function is achieved, the saw blade 7 can be dismounted. Specifically, the saw blade 7 can be bolted to the bottom of the rotating bracket 6 or snap-fitted to the bottom of the rotating bracket 6 for a detachable connection.

As shown in FIG. 1, a part of the air duct 9 is erected on the support 3, the telescopic arm 4, and the rotating bracket 6. During the mounting, the air duct 9 in the present embodiment can be adhered to the outer wall of the support frame, the telescopic arm 4, and the rotating bracket 6 so as to play the role of fixing the position of the air duct 9, or can be fixed to the support frame, the telescopic arm 4, and the rotating bracket 6 via a thin rope, and can also play the role of fixing the position of the air duct 9.

In this embodiment, the controller controls the rotation of the first motor 5, the second motor, the third motor, and the blower 8 to achieve emasculation and/or pollination. When the controller controls the first motor 5, the saw blade 7 rotates to perform emasculation. When the controller controls the second motor, the position of the air blowing portion 10 is adjusted to blow pollens to improve the pollination quality. When the controller controls the third motor, the telescopic arm 4 can move up and down along the support 3 to adjust the height of the saw blade 7. When the controller controls the blower 8, the blower 8 can rotate to generate wind, thereby blowing air to the pollinating maize through the air blowing opening.

In the embodiment described above, the support 3 is movably connected to the base 1 by means of a folding bracket 13 mounted to the support 3, the first end of the folding bracket 13 being hinged to the support 3 and the second end of the folding bracket 13 being hinged to the base 1. When the robot needs to be transported, the support 3 and above components can be laid down on the base 1 by means of a hinge, which is convenient for transportation and has great practical application value.

A breeding method using the breeding robot described above includes steps as follows:

S1: a CCD detector determines the position of emasculated maize and transmits the position to the controller, the controller controlling the walking device 2 to walk to the position;

S2: the controller controls the first motor 5 to rotate the rotating bracket 6 to drive the saw blade 7 to perform emasculation; wherein in this step, the controller also controls the third motor to move the telescopic arm 4 up and down along the support 3 to adjust the height of the saw blade 7;

S3: the breeding robot returns to complete the emasculation;

wherein after 20 days, pollination is performed;

S4: the CCD detector determines the position of pollinating maize and transmits the position to the controller, the controller controlling the walking device 2 to walk to the position;

S5: the controller controls the blower 8 to rotate, and the air blowing portion 10 blows pollens; wherein in this step, the controller may also control the second motor to adjust the position of the air blowing portion 10 to blow the pollen to improve pollination quality; the fourth motor can also be controlled such that the cross bar 12 can perform slow rotation and vibration driven by the fourth motor, and further serve the purpose of shaking off the pollen while the air blowing portion 10 performs blowing;

S6: the breeding robot returns.

It needs to be noted that the relational terms such as "the first" and "the second", and the like herein are merely intended to distinguish one entity or operation from another entity or operation without necessarily requiring or implying any actual such relationship or order between such entities or operations. Furthermore, the terms "comprises", "comprising", or any other variation thereof, are intended to cover a non-exclusive inclusion, such that a process, a method, an article, or equipment that comprises a list of elements not only includes those elements but also includes other elements not expressly listed or elements inherent to such process, method, article, or equipment. An element defined by the phrase "including one" does not, without more constraints, preclude the existence of additional identical elements in the process, method, article, or equipment that includes the element.

The above is only a specific implementation mode of the present disclosure, which enables those skilled in the art to understand or implement the present disclosure. Various modifications to these embodiments will be readily apparent to technicians in the art, and the generic principles defined herein may be implemented in other embodiments without departing from the spirit or scope of the present disclosure. Therefore, the present disclosure is not to be limited to the embodiments described herein, but is to be accorded with the widest scope consistent with the principles and novel features disclosed herein.

What is claimed is:

1. A breeding robot, comprising a base provided with a walking device at a bottom of the base;

wherein a support is movably connected to the base, the support is a hollow cylinder structure, a telescopic arm movably passes through the support, an end of the telescopic arm away from the support is mounted with a first motor, a transmission shaft of the first motor is connected with a rotating bracket, a saw blade is mounted to a bottom side of the rotating bracket, and the saw blade is used for cutting maize tassel;

a blower is further mounted to the base, an air outlet of the blower is connected to a first end of an air duct, and a second end of the air duct is connected to an air blowing portion;

the end of the rotating bracket is mounted with a detector for detecting a position of maize tassel;

wherein a satellite positioning system is further mounted to the base, a controller being provided in the base for receiving an instruction from the satellite positioning system for controlling an operation of the walking device;

wherein the end of the rotating bracket away from the telescopic arm is provided with a second motor connected to the air blowing portion for adjusting an angle of the air blowing portion relative to the rotating bracket;

wherein a third motor is mounted in the support, a rotating shaft of the third motor is connected to one end of a lead screw, and the other end of the lead screw is threadedly connected to the telescopic arm, so that the telescopic arm moves up and down along the support; and wherein the controller is used for controlling a rotation of the first motor, the second motor, the third motor, and the blower to achieve emasculation and/or pollination.

2. The breeding robot according to claim 1, wherein a fourth motor is mounted to the telescopic arm, and the transmission shaft of the fourth motor is connected to a cross bar, the cross bar being arranged transversely for shaking off pollens.

3. The breeding robot according to claim 1, wherein the saw blade is detachably connected to a bottom side of the rotating bracket.

4. The breeding robot according to claim 1, wherein a part of the air duct is erected on the support, the telescopic arm, and the rotating bracket.

5. The breeding robot according to claim 1, wherein a folding bracket is further mounted to the support, the first end of the folding bracket being hinged to the support and the second end of the folding bracket being hinged to the base.

6. A breeding method based on the breeding robot according to claim 1, comprising steps as follows:
- S1: the detector determines the position of emasculated maize and transmits the position to the controller, the controller controlling the walking device to walk to the position;
- S2: the controller controls the first motor to rotate the rotating bracket to drive the saw blade to perform emasculation;
- S3: the breeding robot returns;
- S4: the detector determines the position of pollinating maize and transmits the position to the controller, and the controller controls the walking device to walk to the position;
- S5: the controller controls the blower to rotate, and the air blowing portion blows pollens; and
- S6: the breeding robot returns.

7. The breeding method according to claim 6, wherein a fourth motor is mounted to the telescopic arm, and the transmission shaft of the fourth motor is connected to a cross bar, the cross bar being arranged transversely for shaking off pollens.

8. The breeding method according to claim 6, wherein the saw blade is detachably connected to a bottom side of the rotating bracket.

9. The breeding method according to claim 6, wherein a part of the air duct is erected on the support, the telescopic arm, and the rotating bracket.

10. The breeding method according to claim 6, wherein a folding bracket is further mounted to the support, the first end of the folding bracket being hinged to the support and the second end of the folding bracket being hinged to the base.

* * * * *